United States Patent [19]
Gehret et al.

[11] Patent Number: 5,665,370
[45] Date of Patent: Sep. 9, 1997

[54] COMPOSITIONS CONTAINING COCKROACH AGGREGATION PHEROMONES, THEIR PRODUCTION AND USES

[75] Inventors: Michael J. Gehret, Lititz; Frank N. Chang, Dresher, both of Pa.

[73] Assignee: Temple University Of The Commonwealth System Of Higher Education, Philadelphia, Pa.

[21] Appl. No.: 393,090

[22] Filed: Feb. 22, 1995

[51] Int. Cl.$^6$ ............ A01N 25/10
[52] U.S. Cl. ............ 424/413; 424/405; 424/410; 424/411; 424/84; 424/77; 424/538
[58] Field of Search ............ 424/405, 84, 407, 424/409–413, 538; 43/136, 132.1, 133, 134, 107, 114, 116

[56] References Cited

U.S. PATENT DOCUMENTS

| | | | |
|---|---|---|---|
| 4,337,592 | 7/1982 | Hasegawa | 43/113 |
| 4,608,774 | 9/1986 | Sherman | 43/114 |
| 4,911,907 | 3/1990 | Shimamura et al. | 514/646 |
| 4,945,107 | 7/1990 | Milmetti | 514/473 |
| 5,090,153 | 2/1992 | Mullen et al. | 43/114 |
| 5,123,202 | 6/1992 | Tanisake | 43/131 |
| 5,134,802 | 8/1992 | Cogan et al. | 43/107 |
| 5,167,955 | 12/1992 | Teale et al. | 424/84 |
| 5,238,681 | 8/1993 | Chang et al. | 424/405 |
| 5,271,179 | 12/1993 | Cohen | 43/131 |
| 5,359,808 | 11/1994 | Fitsakis | 43/132.1 |
| 5,384,120 | 1/1995 | Blum | 43/84 |
| 5,401,506 | 3/1995 | Chang et al. | 424/408 |

FOREIGN PATENT DOCUMENTS

| | | |
|---|---|---|
| 46-18518 | 5/1971 | Japan. |
| 53-138880 | 12/1978 | Japan. |

OTHER PUBLICATIONS

Koehler et al., Handbook of Pest Control, Franzak and Foster Co., Cleveland, OH (1990).

PCT International Search Report, issued Aug. 2, 1996 in corresponding PCT Application No. PCT/IB96/00219.

*Primary Examiner*—Neil S. Levy
*Attorney, Agent, or Firm*—Ratner & Prestia

[57] ABSTRACT

An insecticidal product comprises a solid substrate impregnated with sterile cockroach aggregation pheromones, a sterile insecticidal composition comprises a solvent extract of the product, which may be in solution, and an insect attractant product comprises a solid substrate having the composition partially or fully coated thereon. The product and composition of the invention may be utilized in the manufacture of insect traps provided with a hollow receptacle and an opening, and optionally, a cover. An insect trap may comprise a hollow receptacle with a slippery internal surface to prevent the exit of the insects, and an opening, and optionally, a cover. The present products are particularly suitable for trapping insects, such as cockroaches.

15 Claims, 1 Drawing Sheet

FIG. 1

COMPOSITIONS CONTAINING COCKROACH AGGREGATION PHEROMONES, THEIR PRODUCTION AND USES

BACKGROUND OF THE INVENTION

1. Field of the Invention

This invention relates generally to the production of stable cockroach aggregation pheromone products, active extracts thereof, and insect traps utilizing them. These products are useful in the control of cockroach infestation.

2. Description of the Background

Because of their exposure to unsanitary areas, such as sewers, cockroaches are generally associated with the arousal of many health related problems. Over one hundred different species of disease-causing pathogenic bacteria have been found to be carried by cockroaches. Cockroaches have also been found to carry, in addition, other microorganisms such as viruses, protozoa, and parasitic worms (Cornwell, The Cockroach, vol. 1, (1968)).

The use of certain chemical and food attractants for cockroaches is known. Among them are starch, sugar, and fatty acids, such as myristic acid, and palmitic acid and esters of these fatty acids (Japanese Patent Publication No. 44-320). Other chemicals, such as derivatives of naphthalene (Japanese Patent Publication No. 61-69701 and 61-72702); alkylphenol or alkylphenylamine (U.S. Pat. No. 4,911,907), which are specific for male cockroaches, and furanose derivatives (U.S. Pat. No. 4,945,107) have been suggested. Most of the substances, however, have been shown to have low activity and had to be used in extremely high concentrations. In addition, a method for controlling cockroach infestation has also been proposed, which relies on exposing the cockroaches to irradiation with ultraviolet rays. For example, ultraviolet light of longer wavelengths and below 291 nm were utilized in an on and off manner for 15 min. each, for a total time of 9 to 96 hours. This method is said to also inhibit the formation of ootheca. However, this method of controlling cockroaches is expensive and difficult to implement except in specific instances.

Several cockroach traps are now commercially available. Most of these traps, however, are rather ineffective because they do not contain effective cockroach attractants. Such is the case of sticky traps and traps containing boric acid bait.

Aggregation pheromones are produced by many cockroaches, such as the American cockroach or *Periplaneta americana*, the oriental cockroach or *Blattela orientalis*, and the German cockroach or *Blattela germanica*, among others. The production of these pheromones induces the cockroaches to aggregate locally (Bell et al, J. Kans. Entomol. Soc. 45: 414 (1972). The aggregation pheromone composition produced by the German cockroach has been reported to contain over 150 different chemical compounds (Fuchs et al, Z. Angew. Entomol. 99: 499 (1985)). Several components of the aggregation pheromone composition produced by the American cockroach have also been identified (Koehler, et al, Handbook of Pest Control, Franzak and Foster Co., Cleveland, Ohio (1990)). However, they were found to be very volatile and extremely expensive to produce. Thus, no method for producing large quantities of stable aggregation pheromones is currently unavailable.

Aggregation pheromones had previously been extracted from the feces of German cockroaches (*Blattella germanica*) using Freon 11 as a solvent (Fuchs et al., Z. Angew. Entomol. 99: 499 (1985)). The use of fecal materials from cockroaches not only poses logistical problems, but is also uneconomical. The Freon 11 extracts of cockroach feces have been characterized. They contain chemicals which can be roughly classified in two groups. The first group comprises volatile substances that attract cockroaches while the other group comprises non-volatile substances having arresting activity, e.g., act to aggregate the cockroaches.

An ideal attractant should not only attract cockroaches in low concentrations but, once cockroaches are attracted to the site, should have a prolonged stationary effect on the insects. However, up to the present time, even though aggregation pheromones were known to be present in the feces of cockroaches, the extraction of these pheromones has been impractical and uneconomical because it requires large amounts of fecal material and poses sanitary problems.

U.S. Pat. No. 4,337,592 to Hasegawa discloses the extermination of cockroaches with ultraviolet radiation. In addition, the prior patent describes the elimination of aggregation pheromone activity by ultraviolet irradiation of insect feces and pheromones extracts from *P. americana, P. fuliginosa, P. austrasiae, B. germanica*, and *N. cinerea*. In the prior art patent, pheromones were obtained by extraction from cockroach excrement with methanol, and then irradiated with a holder type ultraviolet germicidal lamp.

U.S. Pat. No. 4,608,774 to Sherman discloses a gravity operated cockroach trap having a rectangular funnel-like interior chute, with walls arranged at an angle greater than 10° and preferably 44° to 45° so that the insect on the incline will be drawn by gravity into the receptacle. In one of the embodiments, the prior patent contemplates coating the chute's surfaces with silicone or vaseline. These are solid lubricants which are rendered less and less useful as the angle of the receptacle walls increases. When the inclination of the walls is much greater than 45°, the insects are able to scratch the surface of the solid coating and grip onto the solid wall material.

The complex nature of cockroach aggregation pheromone compositions, their instability, and an inability to mass-produce them in large quantities have precluded the manufacture and availability of effective cockroach lure or trap products containing them.

Thus, there exists a need for a low cost, reliable method of manufacturing formulations containing cockroach aggregation pheromones which preserve their ability to attract and arrest cockroaches.

SUMMARY OF THE INVENTION

This invention relates to a sterile product comprising cockroach aggregation pheromones, and to its solvent extracts, that are stable for several years upon storage.

This invention also relates to a method of producing the sterile product and extracts of the aggregation pheromones themselves.

This invention also provides a device for trapping cockroaches, designed to harbor the trapped cockroaches, e.g., so that they may generate fresh aggregation pheromones, which in turn, attract and trap more cockroaches. The present pheromone products may be utilized alone or in combination with currently available cockroach traps or baits to enhance their efficacy.

DESCRIPTION OF THE PREFERRED EMBODIMENTS

The present invention arose during the course of studies on the behavior of cockroaches, during which the inventors unexpectedly discovered that large quantities of aggregation pheromones may be obtained by placing a solid substrate, e.g., cardboard sheets or wood shavings, among others, within cockroach colonies. Because of the porous nature of cardboard and wood, large amount of aggregation pheromones are deposited, and the thus obtained products have been found to be surprisingly stable, e.g., for more than two years at room temperature. The present invention, thus, solves a problem which precluded the commercial availability of aggregation pheromones as cockroach attractants/arrestants.

Two types of pheromones' activity groups were separated by exposure of a pheromones' solvent extract of the invention to basic and acidic resins, and have been characterized further herein. The first type is a group of volatile attractant compounds which was found to be moderately basic and to bind to acidic resins. The second type is a group of arrestants which was found to include compounds of a slightly acidic nature and to bind to basic resins. Several neutral compounds were also found to possess minor pheromone activity.

This invention, thus, provides a novel product, composition, and methods for preparing the product and the composition and their use in the manufacture of insect traps for trapping cockroaches.

In one aspect, this invention provides an insecticidal product which comprises a solid substrate comprising cockroach aggregation pheromones. The substrate may be a matrix capable of having the pheromones embedded therein or it may be a substrate in the form of a layer, onto which the pheromones are deposited, absorbed, adsorbed, sprayed, coated, and the like.

In general, the solid substrate may be made of wood, cellulose, plastic, ceramic, metal, leather, nylon, rubber, paraffin, wax, cotton, foam, fabric, beads, polyester and other polymers, silica, adhesive tapes, and plaster, among others. The solid substrate may be a porous or a non-porous polymer, such as polymers of polypropylene, polyethylene, polyvinyl, polyurethane, and polystyrene polymers, among others.

Preferred among the solid substrates are wood and cellulose derivatives, because of their porous nature which permits the absorption, adsorption, or deposition of the aggregation pheromones produced by the insects. Most types of wood substrates which are commercially available are suitable for use herein, such as wood chips, flakes, shreds, powder, saw dust, veneer, plywood, hardwood, softwood, fiberboard, particleboard, gypsum, mendeboard, waferboard, and strandboard, among others. Examples of cellulose substrates are paper such as wax paper, printing and writing paper, and paper towels, cardboard, fibers, cork, cellophane, cellulose derivatives such as methyl cellulose, ethyl cellulose, hydroxypropyl cellulose and cellulose membranes, and many others that are commercially available.

The insecticidal product of this invention may be supplemented by the addition of a further substrate provided with a sticky surface, such as glue or other sticky substances utilized in current insect traps, and/or other insecticidal agents. Examples of insecticidal agents currently in use are boric acid, borates, various types of nematode compositions, such as those described in U.S. Pat. No. 4,615,883 to Nelsen et al., entomopathogens including bacteria, e.g., B. thuringiensis, viruses such as those described in U.S. Pat. No. 3,541,203 to Fogle and Peyton, and baculoviruses, fungal pathogens, and the like, insect growth regulators (IGR), botanical and chemical insecticides such as pyrethroids, organophosphates, carbamates, and chlorinated hydrocarbons, among others, and chitin synthesis inhibitors, known in the art. These insecticidal agents may be generally provided in solid or liquid form, as well as in the form of a gel, paste, and the like, as shown for example by U.S. Pat. No. 5,141,744 to Chang et al.

The insecticidal product of the invention is generally obtained by placing an appropriate substrate within a cockroach colony with food and water, collecting the pheromones deposited on the substrates, and sterilizing, for example, $\gamma$-irradiation to prevent germ growth. This is a remarkable advantage over prior art insecticidal preparations containing pheromones, that mostly relied on insects' feces. As is know in the art, insects feces are generally contaminated with pathogens, and this becomes a problem for commercialization. Optionally, most of the feces are removed after the substrate(s) are collected.

Sterilization may be effectively carried out by irradiation with gamma-rays, X-rays, ultraviolet rays, and microwaves, as well as by electron bombardment. The aggregation pheromones product and extract of this invention may also be sterilized by exposure to low temperatures, plasma sterilization, and/or by sterilization with gases such as ethylene oxide and the like. The irradiation conditions for the product and the extract of the invention may be adjusted in terms of the intensity of the irradiation source, and the time of exposure, to ensure that the activity of the pheromones is preserved. Preferably, the irradiation of the product or the extract of the invention is conducted for about 10 sec. to about 2 hrs., and more preferably about 10 min. to 1 hr. Prolonged irradiation, e.g., more than about 9 hrs., and even more than about 5 hrs., with, for example, ultraviolet rays, however, must be avoided.

The insecticidal product of the invention may be packaged in unit form or in packages of several units, and may be sterilized prior to, or after packaging in a sealed container. The product may be sold in large numbers or as individual units contained in, e.g., boxes. The insecticidal product may be sealed in a package either as a unit or in groups of, for example, 2, 5, 10, or more units, preferably in a sealed shrink-wrap package.

This invention also provides an insecticidal composition, comprising a solvent extract of the product of the invention described above. This composition may contain different amounts of the aggregation pheromones obtained from cockroaches. There is, clearly, no limit to the amount of pheromones that may be present in the solvent extract, except for their own solubilities in the solvent.

The insecticidal composition may be prepared by extraction of the substrate embedded with the aggregation pheromones, after removing substantially all feces, with a variety of solvents, including aqueous and organic solvents, and mixtures thereof. Examples of organic solvents are aliphatic alcohols, hydrocarbons, halogenated derivatives, aldehydes, ketones, ethers, carboxylic acids, and esters thereof, among others, and particularly the lower members of these solvents, e.g., the ($C_1$–$C_{10}$) compounds, and in the case of the alcohols, ($C_2$–$C_{10}$) aliphatic alcohols, since methanol is harmful to humans. Preferred solvents are moderately polar solvents, including those of a slight acidic and basic nature. Polar solvents tend to extract both acidic and basic-type components whereas basic solvents tend to extract to a greater extent the acidic pheromone components and acidic solvents tend to extract to a greater extent the basic pheromone components. Thus, the pheromones may be extracted with the aid of solvents ranging from a polar solvent such as water to non-polar solvents such as hexane, because of the multicomponent nature of the composition. The aggregation pheromones are conveniently extracted from the materials used as bedding or layering, with either aqueous or organic solvents, after separating the fecal materials therefrom.

Preferred organic solvents are ethanol, preferably about 70 to 95% ethanol, and isopropanol, both of which are sterilizing solvents and commonly used as topical antiseptics. Because of their antiseptic and sterilizing abilities, the non-sterile aggregation pheromones deposited, absorbed or adsorbed onto the solid substrates may be directly extracted with these organic solvents to produce sterile aggregation pheromones extracts without prior sterilization as indicated above. In addition, ethanol and propanol are examples of solvents that are not known to be harmful to humans, contrary to, e.g., methanol. Other solvents that possess antiseptic properties, which may also be used to extract non-sterile and sterile aggregation pheromones from solid substrates include formalin, sodium hypochlorite, propylene glycol, sodium benzoate, nonoxynol, glutaraldehyde, bennzalkonium chloride, chlorhexidine, phenol, paramonochlorophenol, diglycidyl ether, mixtures thereof, mixtures thereof with ethanol and/or propanol, and mixtures thereof with other chemicals commonly used as preservatives.

The composition of the invention may be utilized as the original extract, or the solvent separated from the pheromonal composition and a different formulation prepared in the form of a solution or suspension in a suitable medium, or mixed with or absorbed onto a suitable carrier or diluent. Thus, the present composition may be used in liquid or solid form. In addition, other ingredients may also be utilized such as additives including emulsifiers, suspending agents, dispersing agents, spreaders, stabilizers, anti-oxidants, and the like. The pheromone composition of this invention may either be mixed with or placed proximal to biological or chemical insecticides. The insecticidal composition may be provided in liquid form as well as in solid, powder, gel, paste, semi-liquid, and semi-solid forms, among other forms. The preparation of different forms of the composition is known in the art and need not be explained in great detail herein. For example, the solid form of the composition may be obtained by evaporation of the solvent utilized in the extraction of the pheromones, and the gel and paste forms as described in the art.

The insecticidal composition of this invention containing aggregation pheromones may be formulated in various forms such as dust, powders, and with the aid of a carrier into granules, tablets, adhesive tapes, and the like.

Figure 1:
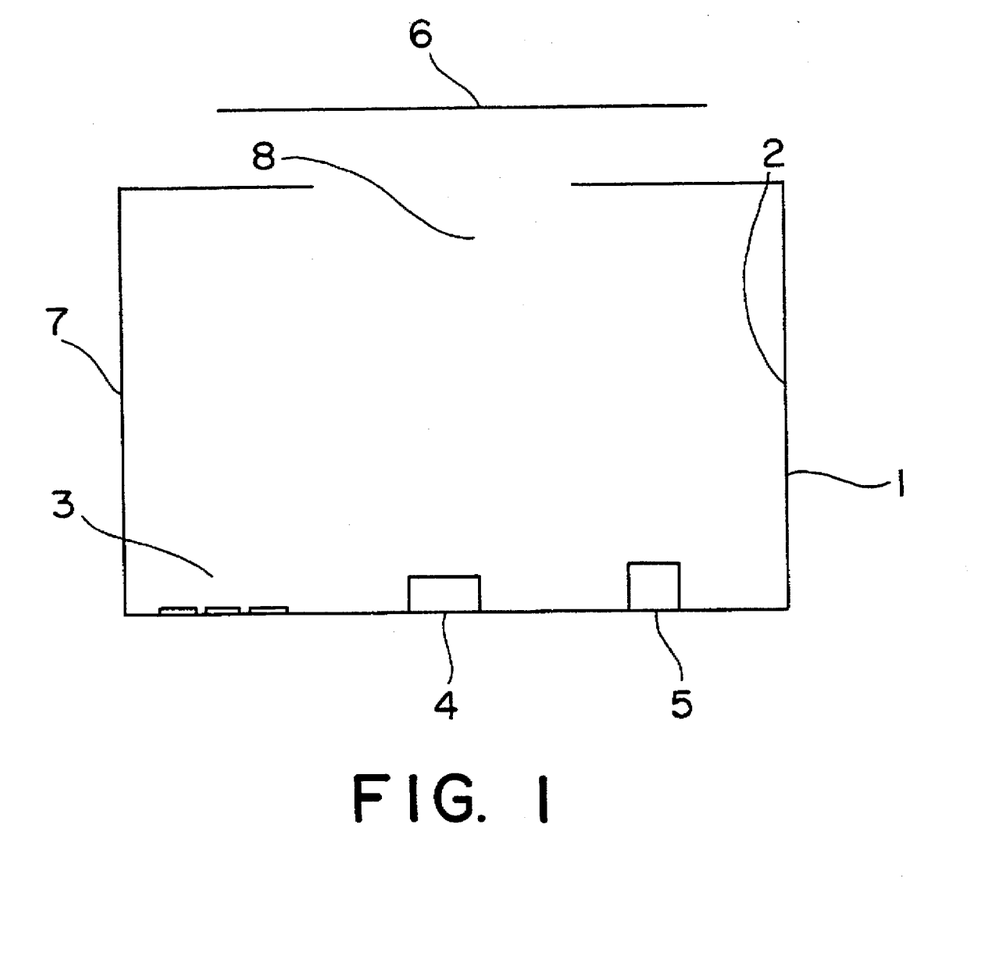
The FIGURE shows a schematic representation of one embodiment of the insect trap of the invention.

In another aspect, this invention provides as shown schematically in FIG. 1 an insect trap 1, comprising a hollow receptacle 7 provided with an internal surface 2 and an opening 8 for receiving insects, such as cockroaches. The receptacle may optionally be provided with a cover 6. The internal surface 2 of the receptacle 7 is provided with the product of the invention 3 affixed to the internal surface 2 of the receptacle 7. As further exemplified in FIG. 1, receptacle 7 of trap 1 includes an opening 8 through which the insects may enter, and placed, e.g., at the bottom of the internal surface 2 is the solid substrate 3 impregnated with the aggregation pheromones and/or extract thereof. In the embodiment shown in the FIGURE, the trap also contains insect food 4 and water 5. In one preferred embodiment, the insect trap is sterilized, preferably by γ-irradiation. However, other types of sterilizations compatible with the materials utilized will also be suitable. In another embodiment, the insect trap is contained in a sealed envelope or package, and it may be sold in unit form or as packages, e.g., 2, 5, 10, or more traps. In a more preferred embodiment, the insect trap, in the form of one or more units, are packaged in a shrink-wrap package, optionally in sterile form.

The insect trap may be provided with a slippery area around its opening and/or the internal surface surrounding the opening and/or even covering a portion or the entire internal surface of the receptacle, to impede the exit of the cockroaches from the trap. The internal surface of the trap is made slippery, preferably by spraying or coating thereon a liquid lubricant, such as liquid petroleum distillates, e.g., WD-40®, silicones such as tin-catalyzed silicones, platinum-catalyzed silicones, oils such as vegetable oils, crop oils and mineral oils, lecithin, polymers such as tetrafluoroethylene, and tetreafluoropropylene polymers and mixtures thereof, e.g., Teflon®, and pyrrolidone polymers such as polyvinyl pyrrolidone, mixtures thereof, and mixtures thereof with insecticidal agents, and/or attractants.

Food and water sources may also be placed inside of the receptacle. The receptacle itself, in all embodiments, may be made of various materials such as cardboard, plastic, glass, leather, ceramic, wood, cellulose and derivatives thereof, polymers such as polyurethane and the like, cotton, foam, beads, minerals such as silica, or metal, among others. Preferred are cardboard and plastic, particularly for the area on the inside surface of the receptacle where the pheromone extract is placed. In another embodiment, the extract may be deposited on a substrate such as plastic, and placed inside the receptacle, which itself may be formed of a different material. The insect trap may also contain glue or other insecticidal agents such as chemical and botanical insecticides, insect growth regulators (IGR), bacteria, viruses and fungal pathogents, nematodes, and the like, that are known in the art for their insecticidal activity. The insect trap may be provided in unit form or in 2, 5, 10, or more units packaged separately or in groups, preferably in a sealed package, and more preferably in a shrink-wrap sealed package, preferably in sterile form.

In another embodiment, because of the aggregation pheromones' abilities for attracting and arresting the attracted cockroaches, the product of this invention may be utilized to significantly increase the effectiveness of currently available insect traps, such as glue traps or bait stations. The aggregation pheromones' product and extract formulated in accordance to this invention may be placed on various surfaces of the receptacle, e.g., internal or external surfaces, including on top of the glue trap or bait (bait station). The aggregation pheromones composition of this invention may also be mixed or placed proximal to glues or commonly used chemical or biological insecticides. In bait stations, a preferred placement site is on the underside of the top cover, directly facing the bottom compartment containing chemical or biological insecticides. However, other sites are also suitable.

The product, composition and insect trap provided herein may be utilized for trapping insects, e.g., cockroaches, by placing the sterile product, extract composition or insect trap at a site near the insects' environment, allowing the insects to aggregate on and around the placement site, and preventing the insects from escaping from the site.

The preparation of the insecticidal product and extract composition of the invention are exemplified below. A multiplicity of exemplary experimental data are being provided to illustrate the present invention.

This invention also comprises an insect trap comprising a hollow receptacle provided with an internal surface and an opening for receiving insects, which is optionally provided with a cover. The internal surface of the receptacle is partially or fully slippery to prevent the exit of the insects from the trap. The inventors have found this trap to be suitable, by itself, to attract and arrest insects, such as cockroaches, although in lesser numbers than the traps containing either the product or the composition of the invention alone or in combination with other baits, glue of a slippery surface.

Generally, the insecticidal product of this invention may be prepared by placing in a contained environment at least one solid substrate, and optionally cockroach food, water and/or aggregation pheromones, and a cockroach colony, allowing the cockroaches to move freely within the contained environment for a period of time effective to obtain a product containing, among other ingredients, aggregation pheromones, and separating the product embedded with the pheromones from the cockroach colony, and preferably from any feces present.

In one preferred embodiment, the substrate is made of multiple substrates arranged in layers within the contained environment. The layers may be separated by spacers and in some instances, placed on racks for ease of manipulation. A suitable distance within the racks and/or substrate layers is about ⅛ to 1", preferably about ⅛" to +e,fra 6+ee ", more preferably ¼" to 2", and still more preferably about ¼". However, other separation distances may also be utilized. In addition to the multiple layers of substrates, the preparation of the pheromone product may be facilitated by adding a slippery material inside, or around the perimeter, of the contained environment and/or the tank to prevent the exodus of the insects from the contained environment. Among the slippery materials utilized, preferred are liquid petroleum distillates, e.g., WD-40®, silicone-based materials, tetrafluoroethylene and tetrafluoropropylene polymers, e.g., Teflon®, or mixtures thereof, oils such as vegetable and crop oils, e.g., corn oil, peanut oil, olive oil, and the like, slippery polymers such as those of pyrrolidone, and mixtures thereof such as a mixture of corn oil and methyl silicone manufactured by CPC International, among others.

A variety of substrates may be utilized, such as wood, cardboard, ceramic, leather, foam, wax, polymers including plastics, nylon, polyester, rubber, and the like, cotton, silica, and plaster, among others. Preferred is wood in a variety of forms, and more preferred is Eastern white pine wood. In order to prepare large amounts of aggregation pheromones, it is preferable that the cockroaches be allowed free movement within the contained environment, and that they be provided food and water, so that the environment resembles a nesting environment to a great extent. Under these conditions, the cockroaches produce large amounts of pheromones, which are absorbed, adsorbed or deposited onto the solid substrates, in a short period of time. The cockroaches are allowed to move freely within the contained environment for a period of time effective to obtain a large amount of aggregation pheromones. Typically, the period of time may vary between one day and several months, and in some instances, it can be extended to a period of up to a year or several years, if desired.

The slippery material provided herein, provided to impede the exodus of the cockroaches from the trap, is generally a liquid lubricant, which is applied to the inside surface and/or walls of the container. The utilization of solid lubricants, such as solid silicones, Vaseline®, and the like, is only suitable for facilitating the downward sliding of cockroaches down a substrate surface positioned at small angle, e.g., 27° to 45°. However, when the sides of the receptacle are positioned at an angle greater than 50°, e.g., up to a 90° angle or greater, the solid or semi-solid lubricants such as Vaseline®, permit the cockroaches to grip onto the wall and dislodge the Vaseline® during their upward motion to escape. In other words, because of its semi-solid nature, a Vaseline® layer may be easily broken by the cockroach's grip and rendered ineffective to retain them in the receptacle. On the contrary, it was surprisingly observed that when liquid lubricants, such as those described herein, were utilized, the cockroaches were retained and could not escape from the container. Thus, liquid lubricants are particularly well suited for preventing the exodus of the insects when the angle of the coated surfaces exceeds 50°, is greater than 70°, and many times equal to or greater than 90°. The addition of the liquid lubricant, to the inside surface of the receptacle or to the area close to the opening, has a potentiating effect on the production of pheromones by the insects by preventing their exit from a contained environment that simulates cockroach harborage.

Among the slippery, materials, preferred are liquid petroleum distillates, such as those contained in the commercially available spray WD-40®. However, others such as those mentioned above are also suitable.

Finally, the substrate containing the aggregation pheromones is Separated from the cockroach colony, and sterilized for storage, preferably by γ-irradiation. Feces may optionally be removed from the substrates, if desired. However, other sterilization methods may also be utilized.

Similarly, the aggregation pheromones' extract composition of this invention may be produced by placing a substrate having pheromones, produced as described above, absorbed thereon, in contact with a solvent for the pheromones for a period of time effective to obtain a pheromones' extract, and then the extract is separated from the substrate, and sterilized, preferably by γ-irradiation. Typically, the extraction step may be conducted for about a few hours to several years, preferably two weeks to six months. Alternatively, the non-sterile aggregation pheromones deposited on solid substrates may be sterilized using organic solvents with antiseptic properties, such as ethanol and isopropanol, which are also safe for humans.

Having now generally described this invention, the same will be better understood by reference to certain specific examples, which are included herein for purposes of illustration only and are not intended to be limiting of the invention or any embodiment thereof, unless so specified.

EXAMPLES

Example 1

Collection of Aggregation Pheromones

Aggregation pheromones were obtained from cockroaches according to the following procedure. Large bins or containers, e.g., 120 gal capacity, and various shapes, such as square, rectangular, rounded and cylindrical, were loaded with large quantities of cockroaches, e.g., about 100,000, together with food (laboratory chow), and water. These containers were sprayed on the sides with a slippery material, e.g., WD-40®. The slippery edges helped prevent the exodus of the cockroaches and forced them to stay away from the sides of the containers. A cloth liner was placed on top of each container to further prevent the escape of the cockroaches.

Eastern white pine wood shavings and/or boards were then placed in each of the cockroach colonies. The pine wood shavings were placed directly at the bottom of the tank, where the cockroach colony was. The pine boards were stacked on top of one other with ¼ inch thick spacers between them to allow the cockroaches to nest between each set of boards. The cockroaches were allowed to nest on the pine shavings and boards for periods of 3 to 6 months. The chips or boards were collected and used as a source of aggregation pheromones.

Other cellulose-containing absorbent materials such as pieces of cardboard were also used. Porous Synthetic polymers such as plastics, were also found to be effective in trapping cockroach aggregation pheromones.

Example 2

Effect on Cockroach Lethality of Addition of Aggregation Pheromones to Sticky Traps The aggregation pheromones obtained from the German cockroaches in Example 1 were added to commercially available sticky traps and its efficacy tested against the traps alone. A 2.5×1.0×1.0 feet tank covered with a cotton sheet was set up as follows. Laboratory chow and a wet paper towel were placed in the middle of the tank as competitive sources of food and water.

Approximately 30 cockroaches were placed in a 500 ml plastic beaker provided with a lid, where the cockroaches were allowed to acclimate for 1 week, and the beaker was placed in the middle of the tank. The beaker was adapted to simulate a roach nest. Two sticky traps, one with a wood chip containing aggregation pheromones, and one without additives, were then placed on opposite sides of the tank, and the tank was placed in a dark environment and kept in the dark throughout the experiment.

The beaker was then opened to free the cockroaches and allow them to move freely within the tank. After 1 week, the number of cockroaches which stuck to each sticky trap was determined. 5 separate tests were conducted as described and the results obtained are shown in Table 1 below.

TABLE 1

Effect of Addition of Aggregation Pheromones on Cockroaches Trapped

| Test No. | Sticky Trap with Pheromones | Sticky Trap (Control) |
| --- | --- | --- |
| 1 | 28 | 6 |
| 2 | 20 | 8 |
| 3 | 18 | 5 |
| 4 | 20 | 7 |
| 5 | 25 | 5 |
| Cockroaches Caught | 111 | 31 |

As can be seen from Table 1 above, sticky traps containing pheromones were found to capture an average of 22 cockroaches each, whereas only 6 cockroaches were trapped by each of the controls. These results demonstrate that sticky traps with aggregation pheromones are at least 3.5 times more effective in attracting cockroaches than commercially available sticky traps.

Example 3

Long Term Stability of Aggregation Pheromone Product of the Invention

The stability of the product aggregation pheromones deposited on pine wood chips and cardboard was tested as follows. Wood chips and/or cardboard pieces were separately acclimated in German cockroach colonies for a period of 6 months as described in Example 1 above. The wood chips and the cardboard pieces were then removed and placed in separate plastic bags (Ziploc® brand, Dow Chemical, Midland, Mich.), and sealed. The plastic bags were then sterilized by γ-irradiation irradiation at 80 krad. Sterility was tested by the absence of microbial growth by streaking the obtained chips with a sterilized loop on nutrient agar plates and maintained at 30° C. for 7 days.

The chips were then removed from the Ziploc® bags and placed in contact with cockroaches at subsequent dates to determine the presence of attractants in the product. The following results were observed when the wood chips were utilized.

Wood chips were taken out and tested after storage at room temperature for a period of 16 months and the following observed. 6 out of 6 cockroaches were found to aggregate around the γ-irradiated pheromone-containing wood chips within a 24 hour period.

Wood chips were taken out and tested after storage at room temperature for a period of 28 months and the following observed. 5 out of 5 cockroaches were found to aggregate around the γ-irradiated pheromone-containing wood chips within a 24 hour period.

The following results were observed when cardboard pieces containing aggregation pheromones were utilized.

Cardboard pieces were taken out and tested after storage for a period of 6 months at room temperature and the following observations made. 5 out of 5 cockroaches were found to aggregate around the irradiated pheromone-containing cardboard pieces within a 24 hour period.

Example 4

Effect of Addition of Aggregation Pheromones to Sticky Traps on Cockroach Trapping Wood chips containing German cockroach aggregation pheromones, prepared as described in Example 1 above, were also tasted in the field to evaluate the effectiveness of the pheromones. 4 sticky traps, with or without a chip containing aggregation pheromones, were placed in similar locations at sites known to be infested with cockroaches. All traps were monitored after 1 week, and the results observed are shown in Table 2 below.

TABLE 2

Effect on Cockroach Trapping of Addition of Aggregation Pheromones to Sticky Traps (Field Test)

| Test No. | Sticky Trap with Pheromone | Sticky Trap (Control) |
| --- | --- | --- |
| 1 | 7 | 5 |
| 2 | 5 | 3 |
| 3 | 8 | 2 |
| 4 | 40 | 5 |
| Cockroaches Caught | 60 | 15 |

The sticky traps containing a chip with pheromones were found to capture an average of 15 cockroaches whereas less than 4 cockroaches were caught by the controls. These results again demonstrate that sticky traps containing aggregation pheromones are far more effective in attracting cockroaches than regular sticky traps alone.

Example 5

Effect on Cockroach Trapping of Addition of Aggregation Pheromones to Nematode Bait The effect on cockroach trapping of adding the pheromone product of the invention to nematode bait formulation was tested as follows.

Groups of 8 German cockroaches were exposed for 7 days, in separate tanks to nematode baits alone (control), and to nematode baits containing a pheromones chip prepared as described in Example 1, and placed next to the nematode bait stations. The nematode bait containing formulations were prepared according to Chang and Gehret (U.S. Pat. No. 5,238,681). The results obtained are shown in Table 3 below.

TABLE 3

Enhancement of Nematode Bait Trapping by Addition of Aggregation Pheromones

| Nematode Bait | Time (Day) | | | | |
| --- | --- | --- | --- | --- | --- |
| | 0 | 3 | 5 | 6 | 7 |
| | Dead Cockroaches/Total | | | | |
| Control | 0/8 | 0/8 | 2/8 | 4/8 | 4/8 |
| With Pheromones | 0/8 | 2/8 | 5/8 | 7/8 | 8/8 |

The addition of aggregation pheromones-containing wood chips to nematode bait formulations was also found to increase the susceptibility of cockroaches to insect-parasitic nematode bait.

The nematode bait stations (control) Were found to kill only 50% of the cockroaches placed in the large tanks after a period of 7 days. The addition of aggregation pheromones to the nematode bait stations significantly increased the effectiveness of the nematode bait stations, resulting in a 100% killing of the cockroaches in 7 days.

Upon dissection, cockroaches killed with an aggregation pheromone-containing bait stations were found to contain at least 10 times more nematodes than those killed by nematode stations without pheromones. Because of the presence of the aggregation pheromones, the cockroaches were found to congregate around the bait stations allowing a greater number of nematodes to infect the cockroaches.

Example 6

Effect on Cockroach Trapping of Addition of Pheromone Containing Wood Chips to Boric Acid Traps Aggregation pheromone-containing wood chips were also placed within boric acid traps, and found to increase the efficacy of boric acid bait stations for trapping cockroaches.

Boric acid bait stations (control) were constructed in the following way. 0.1 g commercially available boric acid paste (It Works®) were placed in plastic bait stations. In the control traps, only food and water for the cockroaches were added.

In the experimental traps, in addition to boric acid, an aggregation pheromone-containing wood chip was taped to the inside of the bait station, directly over the boric acid paste.

Each bait station was then placed inside a 9"×12" container together with food and water. 5 German cockroaches were then placed within each container, all containers placed in the dark, and the activity of the cockroaches monitored for 8 days. The results obtained are shown in Table 4 below.

TABLE 4

Effect on Cockroach Trapping of Addition of Pheromone-containing Wood Chips to Boric Acid Traps

| Boric Acid Trap | Time (Day) | | | | | |
| --- | --- | --- | --- | --- | --- | --- |
| | 0 | 1 | 3 | 5 | 6 | 8 |
| | Dead Cockroaches/Total | | | | | |
| Control | 0/5 | 0/5 | 0/5 | 3/5 | 4/5 | 5/5 |
| With Pheromones | 0/5 | 1/5 | 2/5 | 5/5 | N/A | N/A |

N/A = Not Applicable

All boric acid bait stations containing a chip with aggregation pheromones were found to kill 100% of the cockroaches within 5 days. This fast mortality rate was attributed to the ability of the pheromone-containing wood chips to cause cockroach aggregation around the boric acid bait stations. The boric acid bait stations without aggregation pheromones were found to take 8 days to kill all of the cockroaches.

Example 7

Preparation of Aggregation Pheromones' Extract

The ability of various solvents to extract aggregation pheromones from solid substrates was examined. The extracts were obtained by cutting into small pieces of about 0.5×3 cm, about 100 g pheromones-impregnated cardboard, and placing the pieces in glass jars containing 500 ml of a solvent, such as water or an organic solvent. The extractions were allowed to proceed for 4 weeks at room temperature. Solvents such as water, ethanol, propanol, isopropanol, butanol, dichloromethane, chloroform, acetone, pentane, hexane and ethyl acetate, among others, were used.

The cockroach attracting/arresting activity of the extracts was determined by spotting 50 µl of extract on pieces of 3 MM filter paper (Whatman), and drying at room temperature. Each of the dried filter papers was placed in a 9"×12" container with 6 adult cockroaches. Water and food sources (lab chow) were provided at the opposite corner of each container, and the containers were placed in the dark. The attraction of the cockroaches to the filter paper was monitored 1 hour after their introduction, and every 24 hours thereafter. Table 5 below shows the results of a representative experiment.

TABLE 5

Effect on Cockroach Trapping of Various Solvent Extracts of Pheromones

| Solvent | Time (Hours) | | | | | | | |
| --- | --- | --- | --- | --- | --- | --- | --- | --- |
| | 1 | 24 | 48 | 72 | 96 | 120 | 144 | 168 |
| Blank | − | − | − | − | − | − | − | − |
| Water | + | +++ | +++ | +++ | ++ | + | + | − |
| Ethanol | ++ | +++ | +++ | +++ | +++ | +++ | +++ | +++ |
| Ethyl Acetate | ± | ± | − | − | − | − | − | − |
| Hexane | + | + | + | − | − | − | − | − |

+++ All 6 cockroaches stay on top of or next to filter paper
++ 4 to 5 cockroaches stay on top of or next to filter paper
+ 2 to 3 cockroaches stay on top of or next to the filter paper
± 1 cockroach stays on top of or next to filter paper Preferred organic solvents were found to be polar solvents, amongst the polar solvents preferred were alcohols, and more preferred were ($C_2$-$C_{10}$) alcohols, such as ethanol, e.g., absolute or 95% ethanol, propanol, isopropanol and butanol. The use of ethanol and isopropanol is preferred because these solvents not only possess excellent extracting ability but also provide antiseptic and sterilizing properties. The aggregation activity of the pheromones may also be extracted with water or aqueous solvents. However, aqueous extracts must be sterilized prior to storage to avoid contamination with microorganisms.

The hexane and ethyl acetate extracts showed activity initially but the increase in extracted activity tapered off after the second day, indicating that these organic solvents may have extracted only hydrophobic and uncharged molecules possessing somewhat lesser activity.

Example 8

Separation and Characterization of Ethanol Extract

The pheromones consist of two main types of components. The first group is comprised of volatile substances that attract cockroaches (attractants) while the other group is composed of non-volatile substances having arresting activity (arrestants).

The two pheromonal types of components were separated by subjecting the ethanol extracts to ion-exchange chromatography with Dowex 50 and Dowex 1 resins. The attractant activity in the ethanol extract bound strongly to the Dowex 50 column, indicating that it is basic in nature. The arrestant activity, on the other hand, bound to the Dowex 1 column, indicating that it is acidic in nature. When the samples tested with two Dowex resins were combined, the cockroaches were attracted very quickly and arrested (aggregated) by the combined sample, indicating that the presence of both components accounts for superior pheromone activity. Some arrestant and attractant acclivities were also found to be present after passing the extract through a Dowex 1 resin followed by a Dowex 50 resin. This suggests that some neutral compounds also had pheromone activity.

In order to separate and characterize the activities of the two types of pheromonal components (attractants and arrestants) present in the ethanol extract, the following method was devised.

2 squares, each ½"×1", were cut out at opposite ends of the top of 3½" high, 3" diameter, Styrofoam® cups. When the cups were inverted and placed in a container, the two cutouts served as entry and exit points for the cockroaches. Two of the above Styrofoam® cups were placed upside down at opposite sides of a 9"×12" container, sterile pheromones' extract was pipetted onto a ½"×1½ filter paper or plastic strip, and dried at room temperature. A control was prepared by pipetting the same volume of ethanol on a filter paper or plastic strip, and dried at room temperature. Water and food (lab chow) sources were placed in the center of the container, and 5 adult cockroaches were then introduced into the container.

Attractant activity was scored as positive when the cockroaches were attracted to the cup containing the extract and remained inside the cup. Arrestant activity was scored as positive when the cockroaches were physically arrested on top of the extract rather than just inside the cup. When arrestant activity alone is tested, it takes a slightly longer time for the cockroaches to locate the arrestant due to the absence of attractant.

The nature of the attractant and arrestant activities was also confirmed by high voltage paper electrophoresis of the extract in 0.05M sodium borate buffer, pH 9.0. The electropherogram was then cut out into ½"×1½" strips, and tested for attractant and arrestant activities as described above. The attractant activity was moderately basic, i.e., migrated to the cathode, whereas the arrestant activity migrated slightly to the anode, indicating that it is slightly acidic. The fraction at the origin (neutral fraction) was also shown to possess some attractant and arrestant activity.

Example 9

Stability of Ethanol Extracts of Aggregation Pheromones

The stability upon storage of the aggregation pheromone extracts was also determined. 100 g pheromone-impregnated cardboard pieces obtained from either a cockroach bin or a colony were cut into small pieces and placed in a glass jar, 500 ml ethanol added, the jar closed, and the extraction allowed to proceed at room temperature, while shaking several times a week.

The cockroach attracting/arresting activity of the extract was tested in accordance with the procedure of Example 8 above every month by pipetting 25 µl extract onto a ½"×1½" black plastic similar to the material used in commercially available cockroach bait stations. Each of the dried plastic pieces was placed inside a cup, and the 2 cups were placed in a 9×12" container provided with 5 adult cockroaches. Water and food sources (lab chow) were also provided. After 2 months of extraction at room temperature, all cockroaches (5 out of 5) had aggregated on top of the plastic strip or stayed near it, inside the cup, within 30 minutes. No cockroaches were near the control plastic strip containing just ethanol. Extracts from this original glass jar were also removed at 2-month intervals up to 18 months and the attracting-arresting activity tested as described above. In all tests, including that of the 18-month sample, all 5 cockroaches were attracted to the inverted cup with the pheromones' extract and aggregated either on the plastic strip or stayed near it, inside the cup, within 30 minutes.

The cockroach pheromone extract, thus, was shown to be stable for at least 18 months at room temperature when stored in the original container.

50 ml ethanol extract were also removed from the original glass jar after 2 months of extraction, and placed in a different container or jar. The stability and activity of the 2-month old extract were also monitored at different time intervals up to 12 months by pipetting 25 µl of the extract onto plastic strips as indicated above. In all samples, including the 12-month sample, all cockroaches were attracted into the inverted cup containing the extract and either aggregated on top of, or stayed near it, inside the cup within 30 min. The control plastic strips with 25 µl ethanol did not attract any cockroaches.

These results indicate that when pheromone-impregnated cardboards are extracted in ethanol for 2 months, the obtained extract contains aggregating pheromones. Furthermore, the pheromone extract was shown to be stable for at least 1 year when stored in a closed container at room temperature.

Example 10

Long-term Stability of Aggregation Pheromones' Ethanol Extract Placed on Solid Support The stability of the aggregation pheromones was examined by applying the ethanol extract onto various solid supports. 50 µl ethanol extract were applied onto pieces of filter paper, cardboard, commercial glue board (Woodstream Corp.), ribbons of various colors such as white, yellow, blue and black, and plastics of various colors such as white, yellow and black. After spotting 50 µl extract onto the supporting materials, each was placed in a Ziploc® bag, sealed and stored at room temperature.

At various time intervals, such as, one, two, three, four and six months, pieces were taken out and tested for cockroach attracting/arresting activity as described in Example 8 above. The activity of extracts was tested using two inverted cups with two openings in each cup. The extracts spotted on filter paper, cardboard pieces, glue boards, and ribbons had activity, but lost it in less than about 2 months. Surprisingly, the extract spotted on the plastic supports, e.g., black plastics, used in commercial bait stations were found to retain their activity for more than 6 months. In the 6-month sample, all 5 cockroaches were attracted into the inverted cup and aggregated either on top of or stayed near the plastic strip containing the pheromone extract, inside the cup, within 2 hours.

This discovery permits the manufacture, for the first time, of insecticidal traps containing pheromones, alone or with other insecticides or glues. This discovery also enhances the effectiveness of commercial bait stations containing boric acid, nematode baits, and other toxicants, by applying, in addition, a pheromone extract, e.g., on the underside of the top cover of a bait station.

Example 11

Enhancement of Cockroach Killing by Addition of Ethanol Pheromones' Extract to Bait Stations Containing Boric Acid Paste The increased efficacy of the pheromones' extract, when placed on bait stations containing boric acid paste was demonstrated under competitive conditions as follows. 9"×12" containers were provided with water (wet paper towel) and food sources (lab chow) placed in the center of the container, and 2 bait stations at opposite sides of the container.

Three tests were run. In Experiment I, 1 trap without bait and 1 with boric acid (It Works®) were utilized. In Experiment II, 2 stations were also utilized, 1 with boric acid (It works®) and the second with ethanol pheromones, extract. Experiment III was conducted with 2 stations, as well, the first station containing no bait, and the second containing boric acid plus an ethanol pheromone extract. The results of these tests are shown in Table 6 below.

TABLE 6

Enhancement of Cockroach Trapping by Addition of Aggregation Pheromones to Boric Acid Bait

| Experiment No. | Material Inside Bait Station | Time of Sampling | |
|---|---|---|---|
| | | 20 min. | 18 hrs. |
| | | Number Attracted Cockroaches | |
| I | None | 0 | 5 |
| | Boric Acid | 0 | 0 |
| II | Boric Acid | 0 | 0 |
| | Pheromone Extract | 4 | 5 |
| III | None | 0 | 0 |
| | Boric Acid + EtOH Pheromones' Extract | 3 | 5 |

* 5 cockroaches per experiment only cockroaches inside stations scored

When the ethanol pheromone extract was applied to the underside of the top cover of a control bait station in Experiment II, 4 cockroaches entered the bait station containing the extract within 20 min. All 5 cockroaches were inside this bait station after 1 hour, and remained there for the rest of the time period examined. This shows that the pheromone extract is an effective cockroach attractant.

When the ethanol pheromone extract was applied onto the underside of the top cover of the bait station directly over boric acid paste in Experiment III, 3 out of 5 cockroaches were quickly attracted (within 20 min) to this station and remained there. After 18 hours, all 5 cockroaches were found in the boric acid plus pheromone-containing station and none in the control station.

The ethanol pheromone extract was, thus, shown to be very effective in attracting cockroaches to a bait station by itself and with boric acid paste. Furthermore, all 5 cockroaches were dead by day 4 in the pheromones' extract plus boric acid stations, whereas in experiments I and II, all 5 cockroaches were still alive on day 4.

Similar enhancement by the ethanol pheromone extract was seen of the effectiveness of bait stations containing nematode formulations instead of boric acid paste.

Example 12

Enhancement of Cockroach Trapping Efficacy by Addition of Pheromones' Ethanol Extract to Sticky Trap The effect on the efficacy of cockroach trapping of adding the ethanol extracts of this invention to sticky traps was tested using the same procedure described in Example 11 above. Aliquouts of the aggregation pheromones' extract were applied onto a ribbon, which was then taped onto one side of a sticky trap (Woodstream Corp.). As in the case of the aggregation pheromone-containing wood chips shown in Table 1 above, the ethanol-extract containing traps attracted over 3 times more cockroaches than the sticky traps.

This indicates that the active components of the aggregation pheromone composition have been extracted and the extract contains most, if not all, of the pheromone activity.

Example 13

Effect of Slippery Boundaries on the Production of Aggregation Pheromones

The nesting of cockroaches in a large confined environment was shown in Example 1 above to produce and accumulate the aggregation pheromones produced by the cockroaches. In this test, a new element was added during the manufacture of cockroach aggregation pheromones. The sides of the containers were sprayed with a petroleum distillate mixture (WD-40®) that remains slippery on the surfaces. The presence of this substance makes the walls so slippery that it prevents the escape of the cockroaches.

The in situ production of natural aggregation pheromones in an environment simulating cockroach harborage was carried out in small containers, made of carton, plastic, synthetic polymers, glass or metal. As an example, the interiors of 2"×2¾" plastic containers without covers, of different shapes such as square, rectangular, round, and cylindrical, were sprayed with WD-40® on all sides to make them slippery. Either γ-irradiated wood chips containing aggregation pheromones or an ethanol extract thereof, along with food and water, were added, and the "slippery" traps were then placed in an area infested with cockroaches.

Under the conditions of the experiment, the cockroaches that were trapped were initially free to move inside the "slippery" container, which thus simulated a cockroach nest. The initial trapping of several cockroaches was found to act as a catalyst to trap many more cockroaches. This resulted in the catching of over 100 cockroaches, which piled up on top of one another. The caught cockroaches occupied sizeable portions of the small containers at the end of 3 weeks. Even though the cockroaches were piling up on top of one another, the slippery edges prevented their escape from the container and facilitated the fall of many newly attracted cockroaches into the trap.

This surprising phenomenon, reflected in an exponential increase in the number of cockroaches trapped over time, is explained by the production of more cockroach pheromones by newly trapped cockroaches. The pheromones, then, act as an attractant for trapping more cockroaches. Thus, a "free environment" trap with slippery walls provided herein has unexpectedly superior characteristics for the effective control of cockroaches through the "self-generation" of fresh aggregation pheromones.

To containers covered with other types of liquid slippery materials, such as corn oil, silicone, corn oil with methyl silicones φ and lecithin (Mazola NoStick®), were added γ-irradiated aggregation pheromones. These were also found to be highly effective for trapping large numbers of cockroaches.

Having now generally described various embodiments of the invention, it should be obvious that many modifications, substitutions and variations of the invention are possible in light of the above teachings.

We claim:

1. A method of producing an insecticidal product, comprising a solid substrate impregnated with sterile cockroach aggregation pheromones, comprising placing in a contained environment at least one solid substrate, cockroach food, water, and a cockroach colony;

allowing the cockroaches to move freely within the contained environment for a period of time effective to allow the solid substrate to be impregnated with aggregation pheromones;

separating the pheromone product from the colony; and further comprising sterilizing the separated product.

2. The method of claim 1, wherein the sterilization comprises γ-irradiation.

3. The method of claim 1, wherein the solid substrate placed in the contained environment comprises aggregation pheromones.

4. The method of claim 1, wherein the solid substrate comprises a plurality of substrates arranged in multiple layers within the contained environment.

5. The method of claim 4, wherein the multiple substrates are held about ¼" apart from one another.

6. The method of claim 1, further comprising coating at least a portion of the contained environment with a slippery material.

7. The method of claim 1, wherein the slippery material comprises a liquid lubricant.

8. The method of claim 1, wherein the substrate comprises wood.

9. A method of producing an aggregation pheromone extract composition, comprising the method of claim 1;

placing the separated insecticidal product comprising a substrate(s) impregnated with the aggregation pheromones in contact with a solvent for the pheromones for a period of time effective to obtain a pheromone extract solution; and separating the extracted substrate(s) from the aggregation pheromone extract solution.

10. A method of producing an aggregation pheromone extract composition, comprising placing in a contained environment at least one solid substrate, cockroach food, water, and a cockroach colony;

allowing the cockroaches to move freely within the contained environment for a period of time effective to allow the solid substrate to be impregnated with aggregation pheromones;

separating the insecticidal product from the colony;

placing the separated insecticidal product comprising a substrate(s) impregnated with the aggregation pheromones in contact with a solvent for the pheromones for a period of time effective to obtain a pheromone extract solution; and separating the extracted substrate(s) from the aggregation pheromone extract solution; and further comprising sterilizing the extract solution.

11. The method of claim 10, wherein the sterilization comprises gamma-irradiation.

12. The method of claim 9, wherein the solvent placed in contact with the substrate(s) is selected from the group consisting of aqueous and organic solvents, and mixtures thereof.

13. The method of claim 12, wherein the solvent is an antiseptic or sterilizing solvent.

14. The method of claim 9, further comprising separating the aggregation pheromone extract from the solvent.

15. The method of claim 14, further comprising adding to the aggregation pheromone extract a carrier.

* * * * *

UNITED STATES PATENT AND TRADE MARK OFFICE
CERTIFICATE OF CORRECTION

Page 1 of 2

PATENT NO. : 5,665,370
DATED : September 9, 1997
INVENTOR(S) : Gehret et al.

It is certified that error appears in the above-identified patent and that said Letters Patent is hereby corrected as shown below:

Column 1, line 64, change "unavailable" to --available--.

Column 4, line 19, change "know" to --known--.

Column 5, line 60, after "receptacle", insert --7--.

Column 6, line 1, change "FIGURE" to --figure--.

Column 7, line 30, after "about 1/8" to", delete "+e.fra7+ee" and insert --6--.

Column 7, line 31, change "¼." to --¼".--.

Column 8, line 27, change "Separated" to --separated--.

Column 9, line 9, change "Synthetic" to --synthetic--.

Column 10, line 35, after "also", delete "tasted", and insert --tested--.

Column 11, line 27, change "Were" to --were--.

Column 15, line 38, change "It works®" to --It Works®--.

UNITED STATES PATENT AND TRADEMARK OFFICE
CERTIFICATE OF CORRECTION

PATENT NO. : 5,665,370
DATED : September 9, 1997
INVENTOR(S) : Gehret, et. al.

It is certified that error appears in the above-identified patent and that said Letters Patent is hereby corrected as shown below:

Column 17, line 20, after "silicones" delete the symbol "φ".

Signed and Sealed this

Tenth Day of March, 1998

Attest:

BRUCE LEHMAN

Attesting Officer

Commissioner of Patents and Trademarks